United States Patent [19]

Greenbaum

[11] Patent Number: 5,407,441
[45] Date of Patent: Apr. 18, 1995

[54] OPHTHALMOLOGIC CANNULA

[76] Inventor: Scott Greenbaum, 8 Tobie La., Jericho, N.Y. 11753

[21] Appl. No.: 41,140

[22] Filed: Mar. 31, 1993

Related U.S. Application Data

[63] Continuation of Ser. No. 893,452, Jun. 4, 1992, abandoned.

[51] Int. Cl.⁶ ..................... A61M 25/00; A61M 35/00
[52] U.S. Cl. .................................. 604/280; 604/283; 604/294
[58] Field of Search ................... 604/51, 55, 239, 264, 604/272, 275, 278, 280, 117, 283, 273, 274, 164, 27, 30, 46, 158, 170, 294, 160, 902, 174, 177; 606/107

[56] References Cited

U.S. PATENT DOCUMENTS

| | | | |
|---|---|---|---|
| 1,198,742 | 9/1916 | Meinecke | 604/278 |
| 2,922,420 | 1/1960 | Cheng | 604/158 |
| 3,611,965 | 10/1971 | Lange | 604/166 |
| 3,774,612 | 11/1973 | Marco | 604/275 |
| 4,753,234 | 6/1988 | Martinez | 606/107 |
| 4,759,746 | 7/1988 | Straus | |
| 4,795,446 | 1/1989 | Fecht | 604/275 |
| 4,808,158 | 2/1989 | Mahurkar | 604/286 |
| 4,808,170 | 2/1989 | Thornton et al. | 604/276 |
| 4,894,657 | 1/1990 | Howes | 604/256 |
| 4,959,057 | 9/1990 | Lang | 604/286 |
| 5,057,098 | 10/1991 | Zelman | 606/107 |
| 5,106,376 | 4/1992 | Mononen et al. | 604/51 |
| 5,197,457 | 3/1993 | Adair | 604/176 |

FOREIGN PATENT DOCUMENTS

| | | | |
|---|---|---|---|
| 1225299 | 8/1987 | Canada | 604/280 |
| 9219143 | 11/1992 | European Pat. Off. | |
| 6808511 | 9/1958 | Germany | |
| 2156223 | 10/1988 | United Kingdom | 604/286 |
| 1706611 | 1/1992 | U.S.S.R. | |

OTHER PUBLICATIONS

Hendrickson Suprapubic Drain, 2 pages, 1938.

Primary Examiner—Randall L. Green
Assistant Examiner—K. M. Reiche
Attorney, Agent, or Firm—McAulay Fisher Nissen Goldberg & Kiel

[57] ABSTRACT

A cannula for applying anesthetic to the eye is a longitudinal housing, having a rounded upper surface that terminates in a blunt closed distal end and a flat lower surface that has an exit port at its distal end and an increased transverse dimension at a proximal end to seal the tissue opening through which the cannula is inserted into the eye.

6 Claims, 1 Drawing Sheet

OPHTHALMOLOGIC CANNULA

This is a continuation of application Ser. No. 07/893,452, filed Jun. 4, 1992, now abandoned.

BACKGROUND OF THE INVENTION

1. Scope of the Invention

The present invention is a cannula for use in ophthalmologic operations. It is particularly useful for injecting anesthetic into the ocular region while eliminating the inherent dangers posed by using a needle to perform a similar function.

2. Description of the Prior Art

The technique for injecting anesthetic into the eye to achieve akinesia, used in approximately 90% of cataract surgeries performed, includes a series of steps. Usually, a blind passage with a sharp needle is performed through the skin below and/or above the eye into the orbital region to introduce anesthetic directly or indirectly into the retro-bulbar space. In a small, but significant, percentage of the time a second blind passage is needed because the first blind passage has not properly accessed the retro-bulbar space. Three to five cubic centimeters(ccs) of anesthetic is used. The protein hyaluronidase is used to help diffuse the anesthetic into the retro-bulbar space in case the space is missed.

It has also been proposed to follow a procedure in which a topical anesthetic is placed on the surface of the eye to minimize sensation. The topical anesthetic allows the surgeon to provide a local anesthetic to the peri-ocular region, to achieve anaesthesia. Once the topical anesthetic has taken effect, a small perforation is made with a sharp needle, piercing the conjunctiva and Tenon's capsule. The region between the Tenon's capsule and sclera, often called sub-Tenon's space, provides indirect access to the retro-bulbar space. Akinesia is achieved shortly after an anesthetic is injected and the operation then ensues.

The use of the needle to access the retro-bulbar space has proven effective. It is used in over 90% of current cataract surgeries. The use of the sharp device in the delicate ocular region, however, may have complications. Since the needle is slid around the globe of the eye, there exists the inherent risk of globe penetration. Furthermore, once the needle directly accesses the retro-bulbar region, there are the further risks of optic nerve trauma and retro-bulbar hemorrhage. Any of these injuries may lead to the complete loss of vision.

During the year immediately prior to this application, approximately 1.4 million cataract surgeries were performed. It is estimated that during the year of this application, this number will increase to approximately 1.5 million, with a continued increasing trend in the coming years. It is also estimated that approximately one out of a thousand of the persons having cataract surgery will be rendered wholly or partially blind due to the use of the needle to inject anesthetic into the retro-bulbar space.

One report of 6,000 consecutive injections indicates that one in 375 had complications of a sort that suggest a direct spread of anesthetic agent to the central nervous system through penetration by the needle of the optic nerve sheath.

Accordingly, an object of this present invention is to provide surgeons with a device which effectively administers anesthetic into the retro-bulbar region while minimizing, if not eliminating, the inherent dangers posed by the presently employed needle method.

A related object of this invention is to provide a device which is low-cost, disposable and easily adaptable to currently used medical equipment.

A further purpose of this invention is to meet the above objectives in a device which can be used with a wide variety of patients.

BRIEF DESCRIPTION

In brief, the device for administering anesthetic to the eye is a small flexible cannula made of thin wall plastic material. One embodiment of the cannula has a length of about 15 millimeters (mm), a width of about 2.5 mm and a thickness of about 0.5 mm. This cannula has a blunt, rounded and curved distal end. An exit port at the distal end of the bottom surface of the cannula provides anesthetic to the patient. A bulbous proximal end is used to seal the opening in the skin of the eye through which the cannula is inserted to minimize back flow of anaesthetic.

DESCRIPTION OF THE PREFERRED EMBODIMENTS

Figure 1:
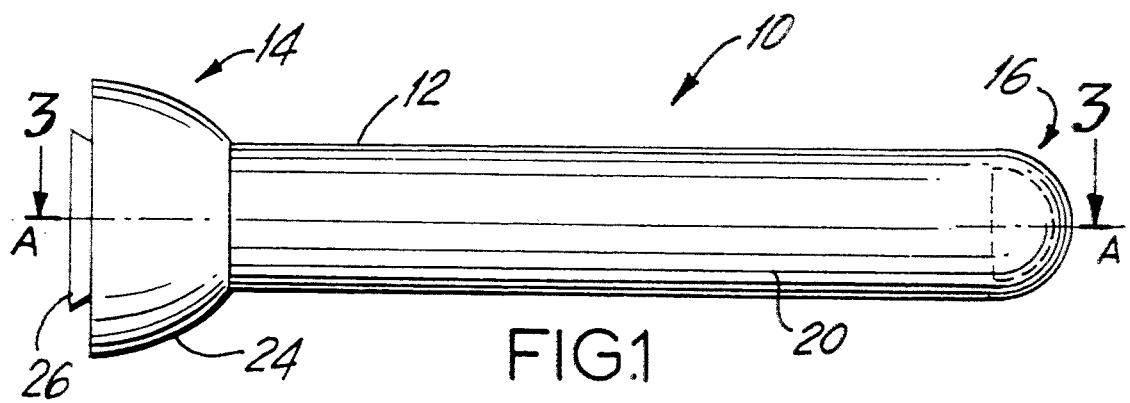
FIG. 1 is a top view of an embodiment of this invention.
Figure 2:
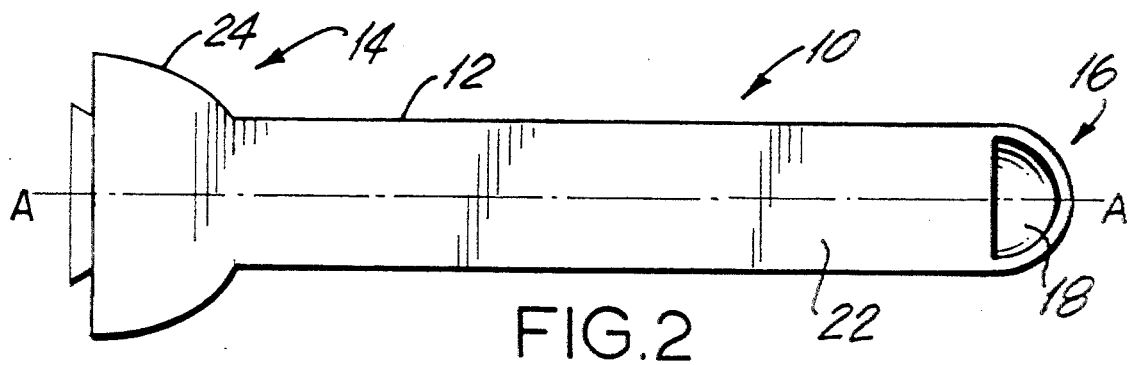
FIG. 2 is a bottom view of an embodiment of this invention.
Figure 3:
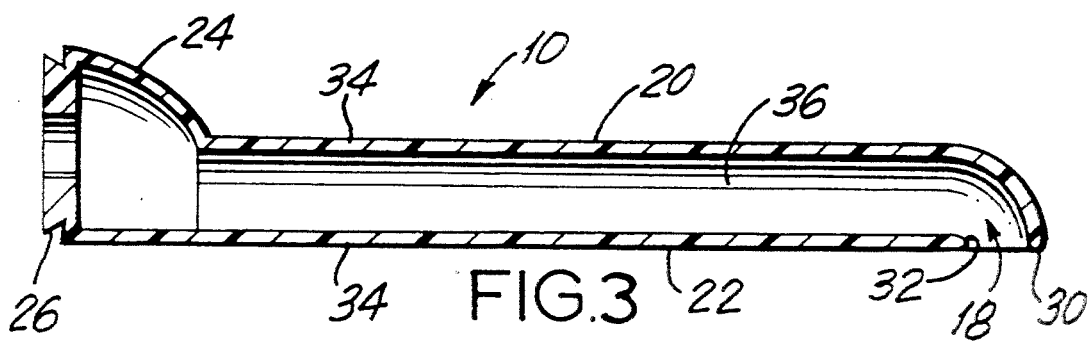
FIG. 3 is a longitudinal cross-section of the FIG. 1 embodiment taken along the plane 3—3 of FIG. 1.
Figure 4:
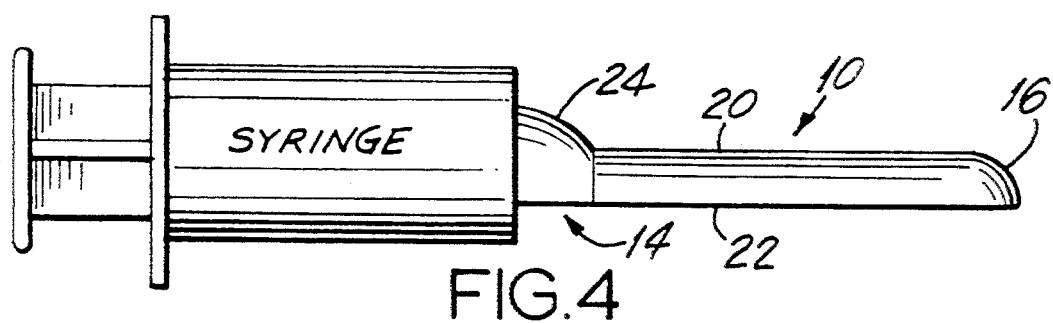
FIG. 4 is a side view of the FIG. 1 embodiment of this invention, showing the cannula attached to a syringe.

The FIGs all illustrate a single embodiment. As shown therein, the cannula 10 has a housing 12, a proximal end 14 into which anesthetic is injected, and a distal end 16 out of which anesthetic flows from a distal port 18. The housing has a longitudinal axis A—A and has a width substantially greater than its height over most of the shaft. The housing 12 has an upper surface 20 and a lower surface 22. The housing 12 defines the passageway 34 through which anesthetic flows. The proximal end of the housing has a bulbous portion 24 which extends out from the upper surface 20 and laterally outward from the main shaft surfaces. The bulbous portion 24 serves the function of sealing or damming the opening in the tissue through which the cannula is inserted to minimize the back flow of anesthesia out of the tissue opening. A standard luer 26 on the proximal end allows for properly hooking the cannula to a standard syringe.

The distal end 16 of the cannula is a blunt rounded zone. The upper surface 20 is curved downwardly to terminate at the edge 30. The upper surface is also rounded along an axis perpendicular to the plane of FIG. 1 so that this distal end 16 is a blunt tip, smooth and curved in all directions.

The lower surface 22 of the cannula terminates at an edge 32. The straight edge 32 and the curved edge 30 define the opening 18 on the bottom surface 22 of the cannula.

A slight curvature of the lower surface 22 might be useful to facilitate having the cannula travel across the sclera portion of the globe of the eye. This curvature would be about an axis parallel to the plane of the page of FIG. 1 perpendicular to the axis A—A.

In one embodiment that applicant contemplates employing, the main shaft of the cannula is about fifteen mm long. The cannula in cross-section has a width of about 2.5 mm and a height of about 0.5 mm. It is contemplated that a polyvinyl chloride plastic material having a thickness of approximately 25 microns (0.025 mm) would be used to form the wall 34 of the housing.

In use, the flexible thin wall material out of which this cannula is made will curve around the globe of the eye. In particular, the bottom surface 22 will be in contact with the globe of the eye. The cannula advances distally along the sclera to lift the Tenon's capsule from the sclera thereby creating what applicant has termed the para-bulbar space.

It is contemplated that the cannula need not extend all the way into the retro-bulbar space to be effective. But what will happen with a short cannula designed so that it does not extend into the retro-bulbar space, is that the hydraulic pressure created by injecting anesthetic out of the port 18 will continue to lift the Tenon's capsule from the sclera causing the anesthetic liquid to flow into the retro-bulbar space. The bulbous proximal end 24 together with the direction of flow created by the downwardly facing port 18 will minimize back flow of anesthetizing fluid and maximize the amount of anesthetizing fluid which flows into the retro-bulbar space. Accordingly, it is contemplated that only between two and three ccs of anesthetic may have to be used instead of the three to five ccs used under present procedures. It should be noted that the contact of the lower surface 22 of the cannula 10 with the globe of the eye will basically prevent anesthetic from flowing back along the surface 22.

The combination of the larger diameter proximal sealing zone 24 and the distal exit port 18 on the bottom surface 22 of the cannula reduces the loss of anesthetic fluid and assures the optimum allocation of anesthetic fluid to the retro-bulbar space where the anesthetic is needed. A blunt tip and low height configuration optimizes the safety for the patient and minimizes the risk of trauma to tissue due to the use of the cannula.

In use, the cannula will be inserted into the eye in an opening made with blunt scissors in the skin of the eye. Using as a reference plane, the plane determined by the axes of the two eyes, the opening would be perhaps twenty-five degrees along the ball of the eye above that plane. The cannula would substantially conform to the sclera for another eighty-five degrees. In doing so, the cannula will have lifted the Tenons from the sclera. The hydraulic pressure of the anesthetic liquid injected will then lift the Tenons from the sclera for another sixty-five degrees and then flow into the retro-bulbar space.

It is contemplated that in another embodiment or usage of this invention a somewhat longer cannula is employed and the retro-bulbar space might be directly accessed by the exit port 18.

However, in either case, it is contemplated that less anesthetic will be needed. Furthermore, because the retrobulbar space is being accessed either directly by the opening 18 or through the para-bulbar space created by the hydraulic flow of fluid, the diffusing chemical hyaluronidase may not have to be used.

Having the exit port 18 at the lower surface 22 instead of in the distal edge of the cannula will reduce the risk of clogging the exit port as the cannula is advanced into the eye.

One object of this design is to provide an instrument that can be used with a wide variety of patients. Some patients will have thick and heavier Tenon's which will serve more effectively to bend the cannula and to help seal against proximal flow. Other patients will have very thin almost non-existent Tenon's for whom the bulbous proximal zone will be of major importance. In general, the Tenon's are the kind of tissue which will tend to protrude in front of the distal end of the cannula and would block a distal end opening. Accordingly, having the exit port on the lower surface of the cannula helps to assure that exit port blockage is minimized.

Accordingly, in order to minimize the risk of tissue damage, minimize the loss of anesthetic and to assure an immediate flow of adequate anesthetic to the retro-bulbar space, this device provides the sealing means at the proximal end of the cannula coupled with the positioning of the port on the lower surface at the distal end of the cannula.

Although this invention has been described in connection with a preferred embodiment, certain adaptations and applications would be known to one skilled in the art. For example, it is contemplated that the primary use of this cannula will be to apply anesthetic to the retro-bulbar region of the eye. But it might also be used for applying antibiotics or steroids. As indicated above, the length of the cannula will be a function of experience showing what the best trade off is between minimizing trauma by having as short a length as possible and assuring that liquid delivered by the exit port 18 will travel into the retro-bulbar space without significant loss of fluid or delay in time.

What I claim is:

1. A cannula for use in applying liquid media to an eye comprising:

a housing having a longitudinal axis, a sealing portion at a proximal end and a main shaft extending from said sealing portion to a distal end, said housing defining a longitudinal passageway through which the liquid media can be applied, said main shaft having an upper surface and a bottom surface, said bottom surface of said main shaft having first and second longitudinal edges which define the width of said main shaft, said longitudinal edges on said bottom surface defining a plane, said bottom surface being contained in said plane, said main shaft having a height, said width of said main shaft being greater than said height of said main shaft, said housing having an exit port, said exit port being located at the distal end of said bottom surface of said main shaft, said distal end of said upper surface of said housing being smooth and rounded, said sealing portion being a bulbous portion of said housing and having lateral dimensions greater than those of said main shaft, said sealing portion having a bottom surface which is continuous with said bottom surface of said main shaft, said bottom surface of said main shaft being planar and said bottom surface of said sealing zone being co-planar with said bottom surface of said main shaft, whereby said bulbous sealing portion serves to block whatever opening is made in tissue for inserting said main shaft into the eye to thereby prevent outflow of the liquid media applied through said cannula.

2. The cannula of claim 1 wherein said housing is a thin wall flexible plastic material.

3. The cannula of claim 2, wherein the ratio of said width to said height is approximately 5.

4. The cannula of claim 2, wherein said width measures approximately 2.5 millimeters and said height measures approximately 0.5 millimeters.

5. The cannula of claim 1, wherein the ratio of said width to said height is approximately 5.

6. The cannula of claim 1, wherein said width measures approximately 2.5 millimeters and said height measures approximately 0.5 millimeters.

* * * * *